United States Patent [19]

Quisenberry

[11] Patent Number: 5,097,829
[45] Date of Patent: Mar. 24, 1992

[54] TEMPERATURE CONTROLLED COOLING SYSTEM

[76] Inventor: Tony Quisenberry, 67 Remington, Highland Village, Tex. 75067

[21] Appl. No.: 495,406

[22] Filed: Mar. 19, 1990

[51] Int. Cl.$^5$ ............................ A61F 7/00; H05B 1/02
[52] U.S. Cl. ................................. 128/400; 219/490; 62/3.2; 62/3.5
[58] Field of Search ................... 128/400; 62/3.2, 3.3, 62/3.5; 165/46; 604/291; 219/297, 490, 327, 328

[56] References Cited

U.S. PATENT DOCUMENTS

| | | | |
|---|---|---|---|
| 3,111,008 | 11/1963 | Nelson | 62/3.3 |
| 3,894,213 | 7/1975 | Agarwala | 219/297 |
| 4,170,998 | 10/1979 | Sauder | 128/400 |
| 4,293,762 | 10/1981 | Ogawa | 219/302 |
| 4,338,944 | 7/1982 | Arkans | 128/400 |
| 4,459,468 | 7/1984 | Bailey | 219/490 |
| 4,476,685 | 10/1984 | Aid | 62/3 |
| 4,494,380 | 1/1985 | Cross | 62/3 |
| 4,844,072 | 7/1989 | French et al. | 128/400 |
| 4,919,134 | 4/1990 | Streeter | 128/400 |
| 4,962,761 | 10/1990 | Golden | 128/400 |

FOREIGN PATENT DOCUMENTS 2417974  10/1979  France ............................ 128/399

*Primary Examiner*—Edward M. Coven
*Assistant Examiner*—Jessica J. Harrison
*Attorney, Agent, or Firm*—Johnson & Gibbs

[57] ABSTRACT

An improved temperature control fluid circulating system for automatically cooling a temperature control fluid in a thermal blanket with a thermoelectric cooling device having a cold side and a hot side when powered by electricity wherein the temperature control fluid is cooled by the cold side of the cooling device and pumped to, through, and from the blanket through first and second conduits. The system includes a device for powering the cooling device with pulse width modulated electrical signals; a device for sensing the temperature of fluid flowing within each of the conduits; a device coupled to the sensing device for calculating from the sensed temperatures an indication of the temperature of the fluid flowing within the blanket; and a device associated with the powering device for modifying the temperature of the fluid by controlling the pulse width modulation of the power supplied to the thermoelectric cooling device.

29 Claims, 5 Drawing Sheets

TEMPERATURE CONTROLLED COOLING SYSTEM

BACKGROUND OF THE INVENTION

1. Field of the Invention

The present invention relates to a temperature controlled cooling system and, more particularly, to a microprocessor controlled fluid circulating system for medical uses.

2. History of the Prior Art

Recent clinical evidence indicates that if the temperature of a body part, particularly a wound site, is lowered a number of therapeutic benefits ensue. First, a lower temperature will reduce swelling and increase the activity of the blood in the wound area to promote healing. Second, a lower temperature at a wound site substantially reduces the pain experienced by the patient. This not only increases the comfort level of the patient but significantly reduces the necessity for the administration of narcotics and other pain medication to the patient's benefit. Third, reduction of the temperature at a wound site increases the flexibility in that region. This is particularly true in the case of a traumatized joint or at the installation site of an artificial joint, where a lower temperature will greatly increase the ability of the patient to exercise the joint. Such treatment can substantially reduce the required period of stay in the hospital.

Initial use of cooling therapy was mainly found in the field of orthopedics. It is now found that post surgical cooling is highly beneficial in the reduction of trauma to the patient. It also increases the rate of healing and reduces the length of a hospital stay. In addition, cooling therapy is also being used in home health care for chronic pain control and to increase joint flexibility and facilitate the rate of healing.

Numerous prior art devices have been proposed for reducing the temperature of a body part in order to achieve the beneficial results obtained thereby. For example, ice packs have long been used to reduce swelling and achieve some of these benefits. In addition, cold packs containing two chemicals, which when mixed together absorb heat (endothermic reactions), have also been proposed as have cooling pads through which a cooling fluid is circulated and cooled by means of a compressor and refrigerant condensing in evaporator coils. Such devices are very inconvenient and contain many inherent disadvantages.

More recently, devices for circulating a cooling fluid through a blanket applied to a patient have also been proposed. Examples of such structures are shown in Kumar U.S. Pat. No. 3,894,213, and Brown U.S. Pat. No. 3,967,027, and Bailey U.S. Pat. No. 4,459,468. The Bailey patent discloses an apparatus which employs a fluid reservoir for containing a substantial volume of cooling fluid, the temperature of which is regulated by thermal modules. The temperature of the fluid in the reservoir is monitored to maintain a selected temperature. The fluid is pumped from the reservoir through a hose system to a thermal blanket which is applied to the patient and back into the reservoir for further cooling. While such a system has been popular in medical applications, it includes numerous disadvantages. For example, a reservoir system, such as that found in Bailey, requires a substantial pre-cooling time in order to reduce the temperature of the relatively large mass of fluid in the reservoir to a desired temperature level. Secondly, such fluid reservoir type systems must also be primed or go through a priming cycle before use to ensure that there is sufficient fluid in the reservoir before performing the cooling operation. Thirdly, the temperature of the reservoir fluid must be monitored and used as the control parameter. This leads to extreme inaccuracy in attempts to maintain a precise control over the temperature applied directly at the wound site. The heat gained by the fluid between a fluid reservoir and a thermal blanket may often be reflected by a temperature increase as much as 10 to 15 degrees. This results in a very inaccurate regulation of the actual temperature at the wound site.

Another problem associated with the applications of very cold surfaces, such as that of an ice pack, directly to a body part is its effect on the skin. The temperature of the ice pack is very cold and can only be left against the skin for a short period of time. Generally, leaving it longer than 30 minutes can result in damage to the skin. It is much more desirable to be able to apply a temperature in a range between 50 and 55 degrees, which is relatively comfortable to the skin, and maintain that temperature for a substantial number of days. This prolonged application insures that the body part is cooled to the inner depth of the bone or tissue of the traumatized area. With an ice pack, cooling only takes place in the subdural area. In a more precisely controlled temperature application, cooling can take place at a deep penetration for an extended period. Thus, it is highly desirable to be able to maintain precise control of the temperature which is actually contacting the tissue of a wound site and then sustain that temperature for a substantial period of time. In this manner the advantages obtained from the use of cold therapy in a medical application can be vastly increased.

It would thus be highly desirable to be able to provide a fully programmable temperature controller for medical applications in which the temperature actually applied to the wound site could be very carefully monitored and controlled. In addition, it would be desirable to be able to produce more immediate cooling and a digital read out of that cooling to a monitoring computer. The variations of the actual temperature of the wound site over a substantial period of time could be used in medical studies and other applications. Such a system could also be programmed to monitor any anomalous conditions in the system such as insufficient amounts of circulation fluid or losses of pressure due to leakage or defective couplings.

SUMMARY OF THE INVENTION

One object of the present invention is to provide a fully automatic, microprocessor controlled system for precisely controlling the temperature of a fluid circulated to a wound site and monitoring the variations in that temperature over time.

Another object of the present invention is to provide a system for circulating a fluid having precisely controlled temperatures through a patient application blanket, which system requires no priming, has a relatively short cool down time and provides an indication in the event of any anomalous conditions within the system.

A further object of the present invention is to provide an electronic controller for a temperature control fluid circulation system which is fully programmable and has a display panel which allows periodic reprogramming of the system and monitoring of the operating conditions thereof.

One aspect of the present invention thus comprises an improved temperature control fluid circulating system for automatically cooling a thermal blanket with a thermoelectric cooling module, the system being of the type where a temperature control fluid is cooled by the cooling module and pumped to, through and from the blanket through first and second conduits. The improvement comprises means for powering the cooling module with a pulse width modulated signal and means for sensing the temperatures of fluid flowing within the conduits. Means are provided for calculating the mean value of the temperatures between the first and second conduits or calculating a set off value from the temperature at the second conduit in order to provide an approximate indication of the temperature of the fluid within the blanket. Means associated with the powering means for modifying the indicated temperature of the blanket are also provided. The cooling module may comprise a thermoelectric cooling device and a thermally conductive cooling block thermally coupled thereto.

In another aspect, the invention described above further includes coupling the thermoelectric cooling device to a power supply, the output of which is controlled by a pulse width modulator for precisely controlling the temperature of the cooling block. The pulse width modulator is coupled to a shift register for controlling the pulse width modulation of the modulator. The cooling block may also include a unitary block having a flow passage formed therein in flow communication with the first and second conduits, the flow passage being of a cross section adapted for facilitating the uniform flow of control fluid therethrough.

In a further aspect, the invention comprises a system for providing temperature controlled fluid circulation through fluid flow circuit. The system comprises a blanket having a fluid passageway therein for applying a temperature to an object. The blanket includes a first conduit for receiving flow of temperature control fluid and a second exit conduit for discharging the flow. Means are connected to the blanket for providing a flow of fluid through the blanket. Means are provided for modifying the temperature of the fluid, the means including a thermally conductive unitary block having a passageway formed therein. The block is positioned in thermal contact with means for modifying the temperature of the block and thereby modifying the temperature of the fluid flowing therethrough. Means are also provided for sensing the temperature of the fluid leaving the block and for sensing the temperature of the fluid returning to the block. Means are provided for calculating the mean value between the temperatures or calculating a set off value from the return temperature in order to provide an approximate indication of the temperature of the fluid within the blanket and means are provided for controlling the temperature modification means in contact with the block to achieve a desired set point value of temperature at the blanket.

BRIEF DESCRIPTION OF THE DRAWING

For an understanding of the present invention and for further objects and advantages thereof, reference may now be had to the following description taking in conjunction with the accompanying drawing, in which.

DETAILED DESCRIPTION OF THE PREFERRED EMBODIMENT

Figure 1:
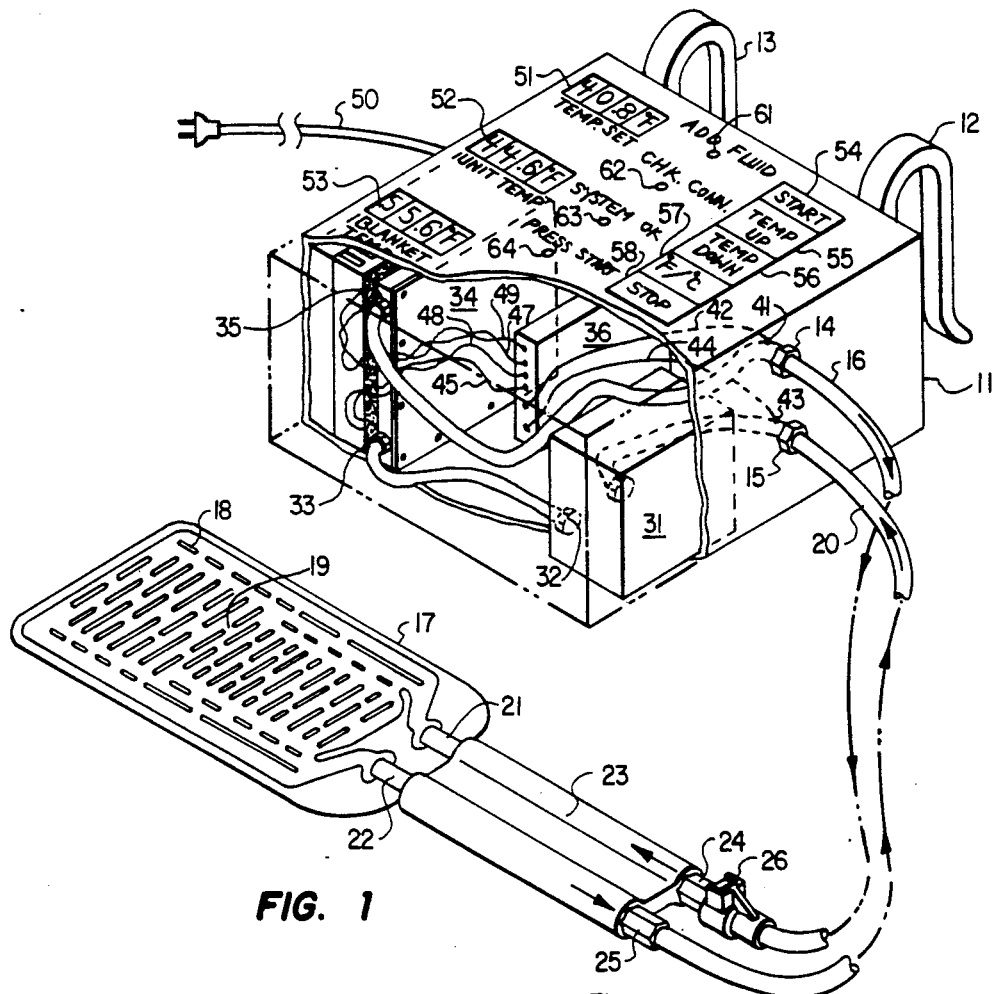
FIG. 1 is a perspective view of a temperature control fluid circulating system constructed in accordance with the teachings of the present invention.

Referring first to FIG. 1, there is shown a perspective view of the temperature control fluid circulating system constructed in accordance with the principles of the present invention. The system includes a mounting cabinet 11 having a pair of hooks 12 and 13 positioned along the rear wall thereof for mounting the cabinet on the foot of a patient's bed. As will be seen below, the features and advantages of the system of the present invention allow it to be very quickly transported, mounted, and put into operation so that it is useful for applying a cool temperature to a wound site.

The cabinet 11 mounts the cooling mechanisms and control circuitry for the fluids used in the present system. A fluid exit connection 14 and a fluid return connection 15 are mounted in one wall of the cabinet 11. A fluid delivery conduit 16 is connected to the exit connection 14 to conduct a temperature control fluid from the cabinet 11 along the conduit 16 into a patient application blanket 17. The blanket 17 is well known in the art and can be formed of opposed sheets of vinyl material which are sealed together at select points 18 and 19 to define a plurality of passageways between the sheets for the circulation of cooling fluid. Preferably one of the two sheets is transparent so that the fluid can be seen circulating through the pad 17. The fluid enters an inlet opening 21, passes through a convoluted path within the pad 17 and exits through a conduit 22. A handle 23 is formed of foam material to facilitate handling of the pad 17. The inlet to the cooling pad 17 is through a bayonet type male connector 24, and the outlet is through a similar bayonet connector 25. The inlet conduit 16 from the cabinet 11 is coupled to the inlet conduit of the pad 24 by means of a self-sealing bayonet coupling 26. This enables the cooling pad 17 to be easily disconnected from the hose 16 and avoid any spillage of fluid from the system. In addition, the pad 17 is preferably provided to the user full of fluid. This eliminates any necessity for priming the system before operation. The fluid is returned from the pad 17 and the coupling 25 through the return conduit 20 into the coupling 15 on the wall of the cabinet 11.

Referring to the components on the interior of the cabinet 11 shown by cutting away the front portion of the cabinet, a peristaltic pump 31 has an outlet opening 32 which sends fluid into an input 33 of a thermoelectric cooling unit 34. The fluid is cooled within the unit 34 and flows from the outlet 35 into the inlet of the connector 15 on the sidewall of the cabinet 11 and then to the pad 17 for application to the patient. The electronic control circuitry is mounted in a control unit 36 to which signals come from various portions of the circuitry for control purposes.

A temperature sensor 41 is coupled in the delivery line of the fluid going to the blanket 17 and a signal to the control unit 36 is coupled from temperature sensor 41 via line 42. Similarly, a second temperature sensor 43 is coupled in the return line from the blanket 17 and a signal from that sensor is coupled to the control unit 36 via the line 44. A machine temperature sensor 45A mounted directly in the fluid path in the thermoelectric cooler itself also senses the temperature of the fluid there and supplies a signal via conductor 45 to the control unit 36. The control unit 36 supplies current to the thermoelectric coolers (TECs) mounted within the cooling unit 34 via conductors 47, 48 and 49.

Referring to the upper surface of cabinet 11, a plurality of displays, control switches and indicator lights are mounted. A first digital display 51 shows the temperature setting of the fluid to be applied to the wound site as set by the operator. A second display 52 displays the actual temperature of the fluid within the thermoelectric cooling unit. The third display 53 displays the calculated temperature of the fluid within the blanket 17 being applied to the wound of the patient. A power cord 50 supplies operating current to the control unit 36 for the operation of the control and power circuitry.

A first control switch 54 is touch actuated and serves to start the operation of the system. A second touch control switch 55 raises the temperature for which the system is set, as shown in display 51. The third switch 56 lowers the temperature at which the system is set as shown in the first display 51. The fourth switch 57 controls the system to switch the temperatures used from fahrenheit to centigrade and back again. Finally, the fifth switch 58 serves to stop the pump and the cooling operation of the system. This function is used by the patient in the event that the blanket 17 must be temporarily removed from the patient when the patient leaves his bed.

The first indicator light 61 indicates the need to add fluid to the system. This is determined by a preselected difference between the set temperature shown in display 51 and the unit temperature shown in 52 indicating the absence of fluid to lower that temperature. Alternatively, the system may include a dual point conductivity probe located in either the delivery or return fluid flow lines to measure the conductivity of the fluid flowing therein. If a high percentage of air is contained in the fluid, the resistance will go up indicating a need to add water to the system. The second indicator light 62 is lit to indicate the necessity for checking a fluid connection on the possibility that a leakage has occurred. The third indicator light 63 is lit when the system is operating properly. The fourth indicator light 64 is lit when the system is ready to begin fluid circulation operation by pressing the start switch 54.

As can be seen from FIG. 1, the system operates by energizing the system and then selecting a preselected temperature in the display 51 by manipulation of the switches 55 and 56. Thereafter, depression of the start switch 54 starts the pump 31 to circulate the fluid through the thermoelectric cooling unit 34 and the conduits leading to and therefrom and into the patient application blanket 17 for application of a cool temperature to the patient. The control system 36 operates to energize the thermoelectric control unit to maintain a very precise temperature of the fluid which is actually being circulated into the blanket. The temperature of the blanket is determined by a calculation of the mean temperature between the temperature of the fluid at the exit conduit 16 of cabinet 11 and the temperature of the entrance fluid returning from the patient blanket 17 at the fluid connection 15. These temperature sensors 43 and 41 provide a much more accurate determination of the actual temperature of the fluid being applied to the patient than the prior art measurement devices detecting fluid reservoir temperature. Alternatively, the system may calculate an approximate blanket temperature by adding an experimentally determined set-off value to the temperature of the fluid in the return conduit 20 measured at sensor 43.

Figure 2:
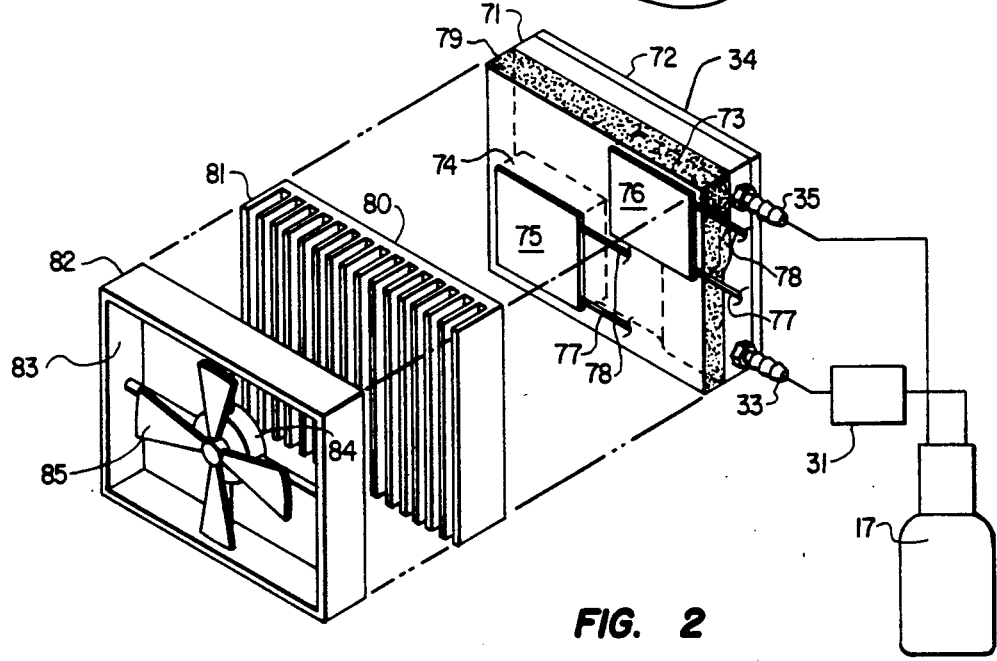
FIG. 2 is an exploded partial perspective view of the thermal electric cooling system incorporated in the system of the present invention.

Referring next to FIG. 2, there is shown a exploded perspective view of the thermoelectric cooling system 34 illustrated in FIG. 1. There it can be seen how entrance and exit conduits 33 and 35 allow fluid to enter into the unitary heat exchange block 71, wherein a serpentine flow pattern has been formed in one surface thereof. The exposed surface of the block 71 will be shown in more detail below to be covered by a plate of relatively thermally insulating material 72. Preferably, the block 71 is formed of a highly conductive metal such as aluminum with the insulating plate formed of a material such as plastic. One side of the block has formed thereon a pair of raised pedestals 73 and 74. The pedestals are preferably formed integrally with the aluminum block 71 and of the same material. The upper surface of each of the pedestals 73 and 74 are placed in contact with the cooling side of a pair of thermoelectric cooling devices 75 and 76. Preferably, a silicon grease or similar material is applied between the surfaces to maximize the heat transfer therebetween.

Still referring to FIG 2, the thermoelectric cooling devices (TECs) 75 and 76 each include a pair of electrical connections 77 and 78 in which current flowing in one direction causes one side of the TEC to cool and the other to heat. Current flowing in the opposite direction causes the reverse side to cool and the other to heat. Such TECs are well known in the cooling art and may comprise thermoelectric devices such as a Melcor model 045-06. As shown in FIG. 2, the cool side of each of the TECs 75 and 76 is disposed adjacent the upper surface of each of the pedestals 73 and 74 of the unitary heat transfer block 71. The hot sides of TECs 75 and 76 are placed against the smooth, planar back surface of a thinned heat sink 80 that is designed to dissipate heat therefrom. The heat sink 80 includes a plurality of elongate fins 81 along the upper surface to increase in the convection heat transfer of heat taken from the hot surface of the TECs. To assist the heat sink 80 in dissipating that heat, a fan 82 is provided to draw air across the fins 81 to assist in the rate of cooling which occurs. The fan 82 may comprise a framework 83 within which an electric motor 84 is mounted for driving a plurality of blades 85 and providing constant cooling to the heat sink 80. The fluid is circulated through the blanket 17 by means of the peristaltic pump 31 which forces fluid into the entrance cavity of the entrance port 33 of the unitary heat transfer block 71 and out the exit port 35 thereof.

As also shown in the FIG. 2, the pedestals 73 and 74 are surrounded by a fixed sheet of foam insulating material 79 into which openings are cut to receive the pedestals 73 and 74. This effectively insulates the cool side surfaces of the pedestals 73 and 74 and prevents thermal inefficiencies due to heat transfer to warmer portions of the structure.

Figure 3:
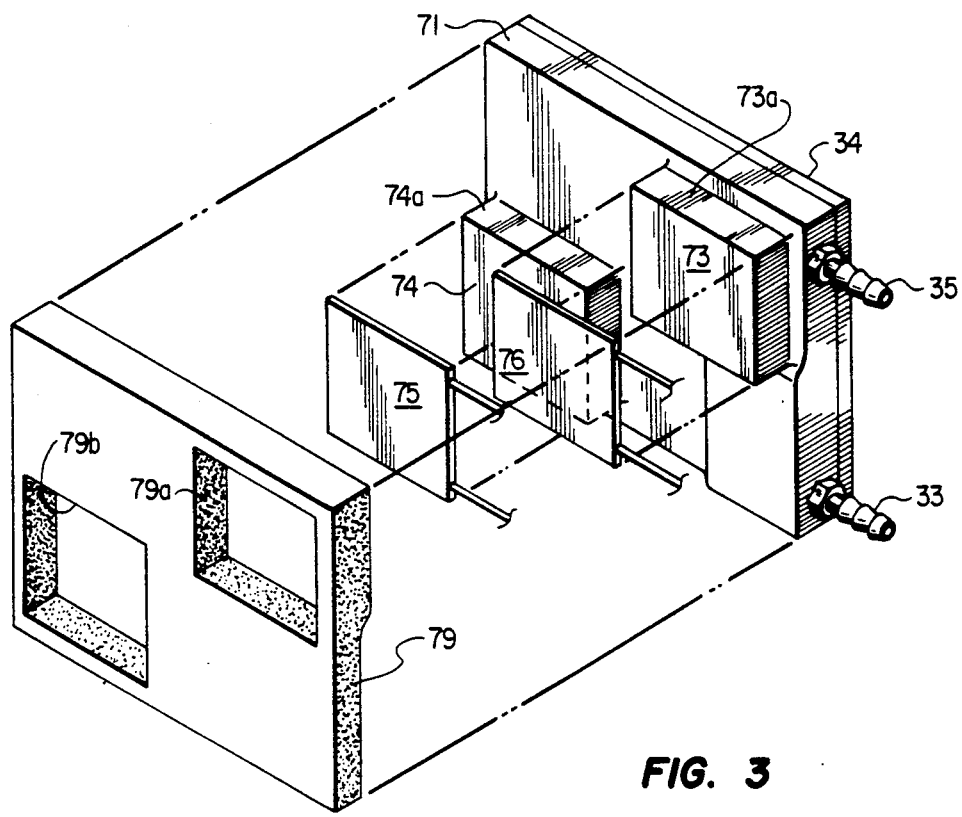
FIG. 3 is an exploded perspective view of the arrangement for mounting thermal electric cooling devices on the heat transfer block shown in FIG. 2.

Referring now to FIG. 3, the heat transfer assembly 34 is shown in exploded view in substantially more detail. There it can be seen how the unitary heat transfer surface of the unitary heat transfer block 71 is integrally formed with the pedestals 73 and 74 extending therefrom. The upper surfaces of those pedestals 73 and 74 are placed in direct contact with the cool sides of the TECs 75 and 76 for efficient heat transfer therefrom. The side surfaces 73A and 74A are insulated for undesired heat transfer by means of the insulated foam structure 79. A pair of windows 79A and 79B are cut in the surface of the foam insulation 79 to receive the pedestals 73 and 74 and protect the side surfaces from undesired heat transfer. Alternatively, a wall can be placed around the pedestals 73 and 74 and an insulated layer can be foamed in place to provide thermal insulation. Further seen in FIG. 4 is temperature sensor 45A mounted directly in the fluid path of the unitary heat transfer block.

Figure 4:
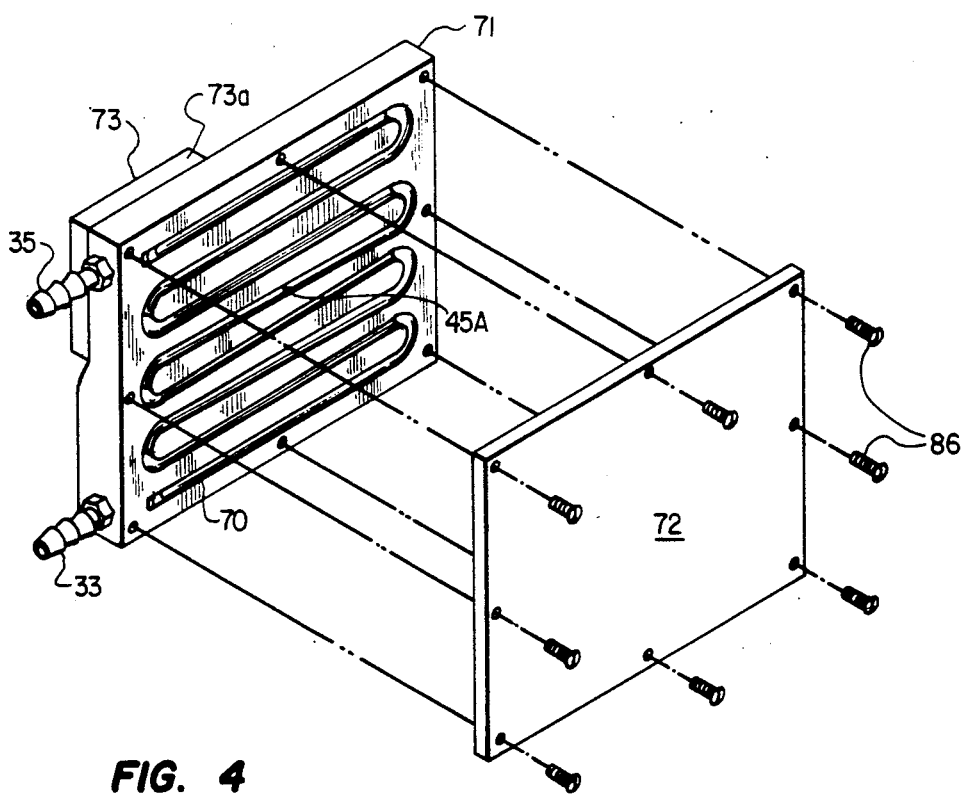
FIG. 4 is an exploded perspective view of the heat transfer block shown in FIGS. 2 and 3.

Referring now to FIG. 4, the unitary heat transfer block 71 is shown in exploded perspective. There it can be seen how the fluid entrance conduit 33 is in fluid connection with a serpentine channel 70 cut directly into the flat surface of the block 71. The channel 70 winds through the body of the aluminum block 71 and is in fluid communication with the exit connection 35 from the block. As can be seen, the channel 70 in the block is formed on the opposite side of the block 71 from the pedestal 73. The upper surface of the channel 70 is closed by means of the thermally insulated plate 72 which is attached by means such as screws 86 to the flat planar surface of the block 71 to form a fluid tight connection and enable fluid to flow through the channel 70 without any leakage. In one embodiment, the plates 72 can be made of clear plastic so that the flow through the channel may be observed. The connections between the plate 72 and the planar surface of the block 73 containing the channel 70 is of course fluid tight to prevent any leakage therefrom.

Figure 5:
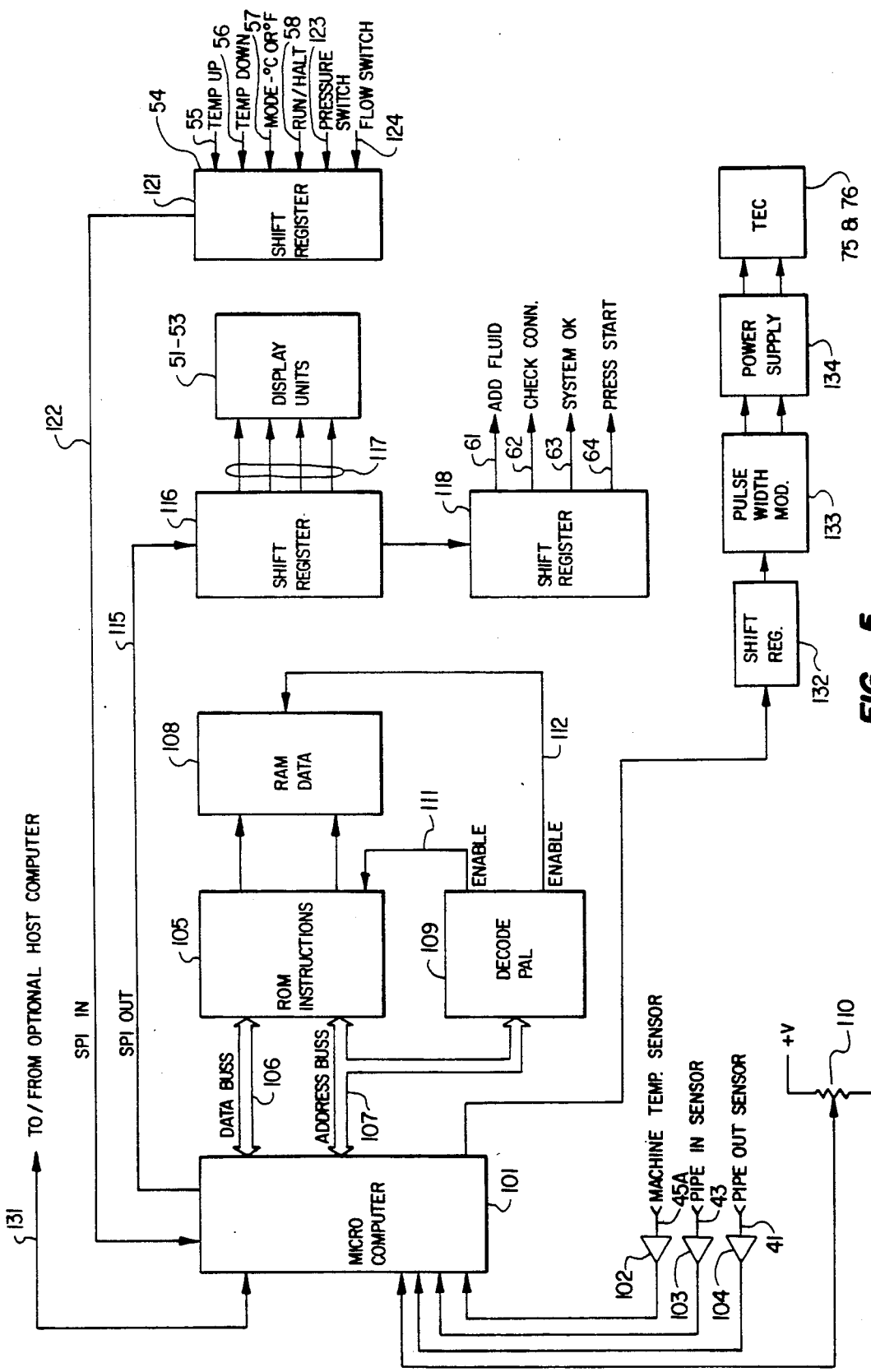
FIG. 5 is a block diagram of the control circuitry used in the system of the present invention.

Referring now to FIG. 5, there can be seen a block diagram of the control circuitry for the system of the present invention. There a microprocessor 101 receives input from a plurality of sensing devices 102–104. The microprocessor may be of different types although a Motorola model 68HC11 microcomputer performs satisfactorily. The external input 102 comes from the machine temperature sensor within the unitary heat transfer block via line 45. The input 103 comes from the fluid flowing into the system as sensed at temperature sensor 41 via line 42 while the signal on input 104 comes from the temperature of the fluid going to the patient blanket as sensed by temperature sensor 43 and communicated via line 44. The microprocessor 101 is connected to a read only memory 105 via a databus 106 and an address bus 107. The system also includes a RAM memory 108 for temporary storage of data within the system. The microprocessor 101 addresses the ROM and RAM memories 105 and 108 by means of an address decoder 109, preferably formed of programmable array logic (PAL), and which provides memory enabling signals to the ROM memory via a bus 111 and the RAM memory via a bus 112. The ROM memory 105 includes certain preprogrammed instructions which are used to supply operating procedures to the microprocessor 101 for operation of the system. An output dataline, SPI OUT, shown at 115, is connected to a shift register 116 for the communication of data to be shown in the various display units 51–53 of the system. The data to be displayed is communicated by the microprocessor 101 into the shift register 116 and thereafter loaded into the display units 51–53 through the lines 117. Similarly, the microprocessor 101 communicates data via line 115 into a second shift register 118 which provides an actuation signal to energize each of the indication lights on the console 11 comprising the add fluid light 61, the check connection light 62, the system ok light 63 and the press start indicator light 64.

Data is communicated by the user to the microprocessor via a shift register 121 connected to the microprocessor via a line 122 designated as SPI IN. Here, signals are communicated into the shift register via the input switches on the console 11. The start switch 54, the temperature upswitch 55, the temperature downswitch 56, the mode control switch 57 and the stop switch 58 provide inputs into the input shift register 121 and then into the microprocessor 101. Similarly, a pressure switch within the system provides an input at 123 in the event the pressure within the circulating fluid system drops below a preselected value. A flow switch 124 provides an input in the event that the flow within the system stops.

The microprocessor provides an output through a conventional RS232 communications bus 131 to or from an optional host computer (indicated but not shown). Such a computer is particularly valuable in the case of monitoring and research work being done with respect to the medical effects of low temperature to a patient.

The microprocessor 101 also provides an output signal through a shift register 132, a pulse width modulator 133 to a power supply 134 which controls the TECs. This enables the system to very precisely control the exact amount of power which is applied to the TECs 75 and 76. The use of a shift register 132 to precisely control the modulation of the pulse width applied through the power supplies 134 enables a very precise control of the temperatures of the cooling applied by the TECs to the fluid to enable a very precise control of the output.

A further input 110 is provided by a voltage divider to precisely calibrate the inputs to the microprocessor at the factory so that the temperatures sensed at the inputs 102, 103 and 104 are very precisely calibrated in the microprocessor to be exactly that temperature based upon precise laboratory monitors.

Figure 6:
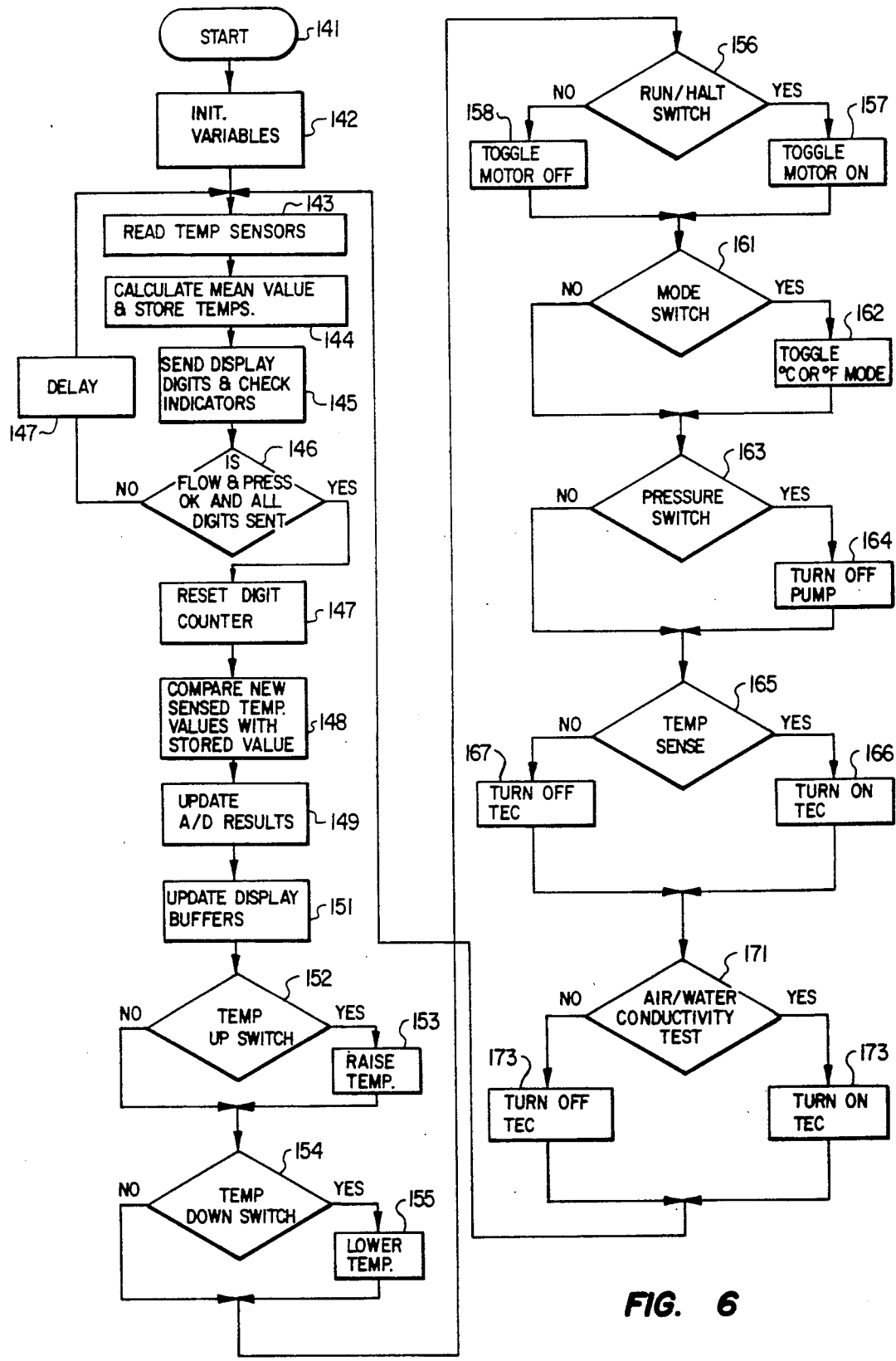
FIG. 6 is a flow chart showing the operation of the system of the present invention.

Referring next to FIG. 6, there is shown a flow chart of the programming which controls the operation of the temperature control fluid circulating system of the present invention. The program starts at 141 and at 142 the microprocessor initializes the different variables within the system. Next, at 143 the program reads the three temperature sensors within the system including the sensor 41 positioned in the outgoing fluid line to the blanket, sensor 43 in the incoming fluid line from the blanket and sensor 45A positioned in the fluid passage in the thermo cooling module itself. The system then calculates the mean value of the temperature between the outgoing and incoming sensors to approximate a temperature value at the blanket itself and stores both the read and calculated temperature values in memory. This occurs at step 144. Alternatively, the system may calculate an approximate blanket temperature by adding an experimentally determined set off value to the temperature of the fluid at the sensor 43 in the return line from the blanket.

At 145, the system sends to the display the digits to be shown in the temperature set value in display 51, the temperature in the thermoelectric module from sensor 45A in display 52, and the calculated value of the blanket temperature in display 53. In addition, at step 145, the system checks the operation of a number of system parameters including whether the pump has turned on and pressure has built within the system below a preselected maximum and above a preselected minimum, whether the TECs have turned on or not because the temperature sensed is below a certain value and whether the connectors are connected because the pressure within the system is below a minimum value. In addition, the system at 146 checks to see whether or not all digits have been sent to the displays 51–53. If any of the parameters investigated at step 146 have not fallen within the required parameter criteria, the system produces a "no" at 146 and enters a delay stage at 147 until the system is fully operational. During this period, the system continues to cycle through reading the temperature sensors, calculating the values and storing them at 144, sending the display digits and checking the indicators at 145 until a yes is achieved at 146. At that point, the system moves to 147 where it resets the digits in the counter, and moves to 148 where the new read temperature sensed and calculated values are compared with the stored values. If there is a difference between them, the system moves to 149 and stores new values in memory for the temperatures. Thereafter, it moves to 151 where it updates the display buffers to display the new values it is now stored. If either the flow or pressure sensors indicate that those parameters are not within a preselected range, the system illuminates the warning lights 61 to check as to whether fluid needs to be added in the event of a low pressure value or 162 to check the connectors in the event that there is a similar low pressure or flow problem.

The system next moves to 152 where it senses whether or not there is a depression of the up temperature switch 55. If so, an internal oscillator within the system ups the set temperature value in 1/10th degree increments per unit of time at 153 until the up temperature switch is no longer depressed. This, of course, changes the values stored for the set temperature and as a result, causes the system to detect that a difference exists between the set value and the calculated blanket temperature value and to accordingly adjust the temperature of the fluid. If, however, the temperature switch at 152 is not depressed, then the system moves to 154 where it senses whether the down temperature switch 56 has been depressed. If yes, the system lowers the set point temperature in 1/10th degree increments at 155. If the down temperature switch has not been depressed as sensed at 154, the system moves to 156 to detect whether or not the run halt switch 54 or 58 have been depressed. If the start switch 54 has been depressed, then the system moves to 157 where the pump motor is toggled on. If the halt switch 58 has been depressed, as detected at step 156, the system moves to 158 which toggles the pump motor off.

Next, the system moves to 161 where it evaluates whether the mode switch 57 has been depressed and, if so, moves to toggle the system at 162 to either the centigrade or fahrenheit mode depending upon which it was previously set. If, however, the mode switch is detected at 161 to not have been depressed, the system moves to 163 where it senses whether a pressure switch has been actuated by the existence of fluid pressure within the system. If pressure is detected, indicating a certain maximum value of pressure within the system, then the system moves to 164 and the pump motor is turned off. If however, the pressure has not built above the preselected maximum value the system moves on to 165 which it determines whether or not the set value of temperature is equal to the calculated blanket temperature. If there is a difference between them and if the blanket temperature is greater than the set point temperature, then the system turns on the TEC at 166 to further cool the fluid. If however, the system detects at 165 that the calculated mean blanket temperature is below the set point value than at 167 the TECs are turned off so that no further cooling of the fluid occurs. At point 171 the system reads the resistivity value to the dual point conductivity probe to determine the relative mixture of air and cooling fluid flowing in the system. If the resistivity is below a selected value there is sufficient fluid in the system so the TEC's are turned on at 172. If, however, the resistivity is above a selected value, there is an excess of air in the system and the TEC's are turned off at 173 and an "add fluid" lamp is illuminated on the console.

As can be seen from the flow chart of FIG. 6, the program driving the system of the present invention constantly monitors the input switches to the system as well as the temperatures existing within the system to very precisely control the temperature of the fluid actually at the blanket. Thus, the system gives very precise and regulated temperature values to the body of the patient to ensure that the desired temperature is maintained over an extended period of time.

Figure 7A:
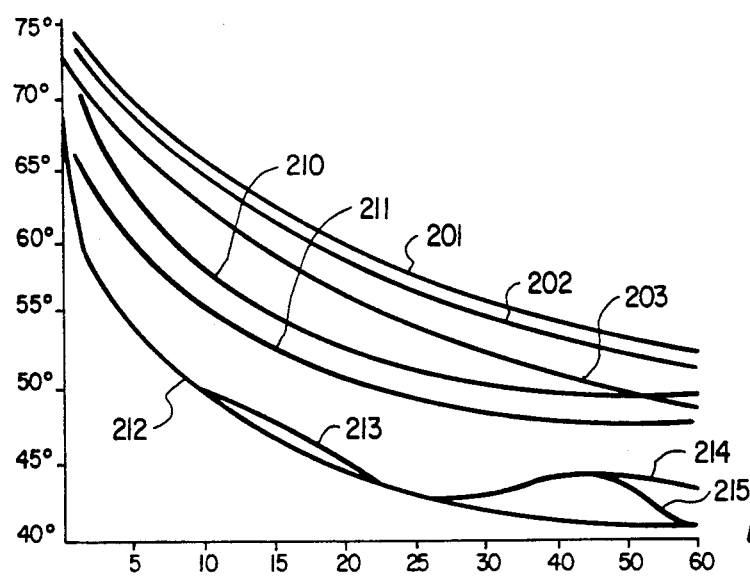
FIGS. 7A-7C are a series of graphs illustrating the improved temperature control at the wound site obtained by the system of the present invention.
Figure 7B:
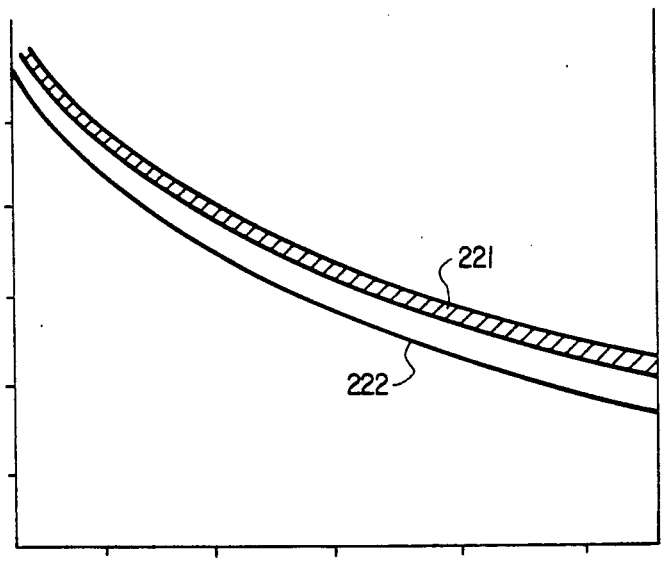
Figure 7C:
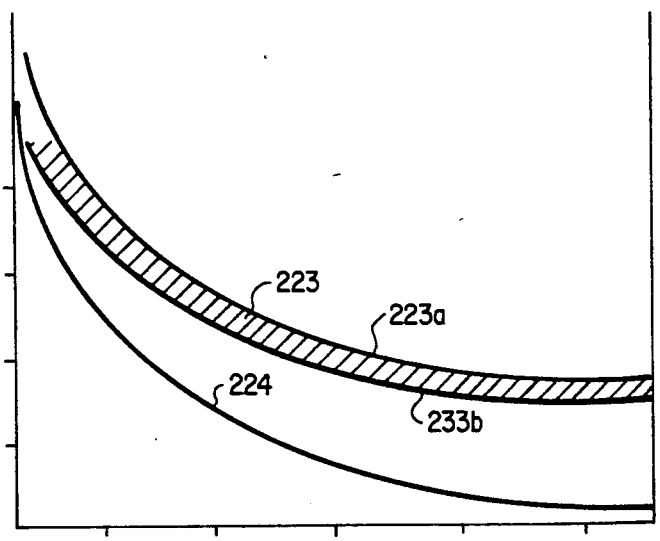

Referring next to FIGS. 7A–7C, there is shown a series of graphs indicating the performance of the system of the invention as compared to a reservoir type system existent in the prior art. Referring specifically to FIG. 7A, there is shown a graph of temperature, given in degrees fahrenheit, over a period of time, given in minutes. The top curve 201 indicates the temperature of the fluid as its return to a fluid reservoir in a prior art system. The next curve 202 shows the temperature of the fluid as it leaves the reservoir of a prior art system going to the blanket. And the third line 203 indicates the reservoir fluid temperature within a fluid storage reservoir over a period of time. The next curve 210 shows the temperature of the return fluid from the blanket (sensor 43) in the system of the present invention indicating the much quicker cooling of the system of the present invention. The second curve 211 indicates the temperature of the fluid going to the blanket from the system of the present invention (sensor 41) while the third curve 212 indicates the temperature of the fluid (sensor 45A) within the actual cooling thermal block of the system of the present invention. It can be seen in curve 212 how the temperature within the block is much improved in rapidity of response than the temperature within the fluid reservoir 203 of the prior art systems. The undulations in the curve 212 shown at 213, 214 and 215 indicate changes in the cooling rate of the parameters at various ambient temperatures within the room. For example, the solid curve at 212 is the performance of the system at an ambient temperature of 76.2° F. The curve at 214 is that performance of the system at an ambient temperature of 84.6°.

Referring to FIG. 7B, the graph demonstrates the range of temperatures between the incoming and outgoing fluids in the prior art. With the inability to precisely know the temperature of the blanket, there is much less ability to control the precise temperature of the blanket. The band 221 indicates the variation of many degrees over this range. The curve 222 is the temperature of the fluid within the reservoir upon which the prior art systems actually control their cooling activity. This indicates the vast differences which exist between the preciseness with which temperature is controlled in the fluid reservoir type system versus the system of the present invention.

Referring to FIG. 7C, the band and range of temperatures in the system of the present invention 223 indicates that the temperatures are lowered in the system much more rapidly than the systems of the prior art (FIG. 7B) and thus require much less initial operation time. The temperature line 224 indicates the actual temperature of the block itself. As discussed above, the temperature control device of the system of the present invention operates based upon the calculated mean value between the temperatures shown by curve 223A and 223B or a set value from the temperature shown in curve 223B which give a very precise indication of the actual temperature at the blanket and thus the system controls based upon that temperature and provides much more accurate indication of temperature at the blanket itself.

As can be seen from the above description of the invention, the system of the present invention gives much more rapid operational conditions within the system than those of the prior art. In addition, the system achieves much more precise control of the actual temperature applied to the body of the patient than those systems of the present invention. Other advantages such as portability and precise temperature control based upon the actual pulse width modulation of the power signals going to the TECs to control the system achieve much greater accuracy than other devices taught by the prior art.

While particular embodiments of the invention have been described, it is obvious the changes and modifications may be made therein and still remain within the scope and spirit of the invention. It is intent that the appended claims cover all such changes and modifications.

We claim:

1. An improved temperature control fluid circulating system for automatically cooling a temperature control fluid in a thermal blanket with a thermoelectric cooling device having a cold side and a hot side when powered by electricity wherein said temperature control fluid is cooled by said cold side of said cooling device and pumped to, through, and from said blanket through first and second conduits, said improvement comprising:
   means for powering said cooling device with pulse width modulated electrical signals;
   means for sensing the temperature of fluid flowing within each of said conduits;
   means coupled to said sensing means for calculating from said sensed temperatures an indication of the temperature of said fluid flowing within said blanket; and
   means associated with said powering means for modifying the temperature of said fluid by controlling the pulse width modulation of the power supplied to said thermoelectric cooling device.

2. The apparatus as set forth in claim 1 wherein said means for calculating an indication of the temperature of said fluid within said blanket includes means for adding a select set-off value to said sensed temperature of said fluid within one of said conduits.

3. The apparatus as set forth in claim 2 wherein said fluid within one of said conduits comprises the fluid returning from said blanket and said set-off value comprises an experimentally determined value.

4. The apparatus as set forth in claim 1 wherein said thermoelectric cooling device is thermally coupled to a unitary heat transfer block connected to said conduits.

5. The apparatus as set forth in claim 4 wherein said powering means comprises a power supply, the output of which is modulated by a pulse width modulator.

6. The apparatus as set forth in claim 5 wherein said modifying means comprises a microprocessor coupled to a shift register for controlling the pulse width modulation of said modulator.

7. The apparatus as set forth in claim 4 wherein said unitary heat transfer block includes a flow passage formed therein and connected to said first and second conduits at its ends.

8. The apparatus as set forth in claim 7 wherein said unitary heat transfer block further includes means for sensing the temperature of said fluid flowing within said flow passage.

9. The apparatus as set forth in claim 1 wherein said calculating means comprises means for calculating an indication of the means value of said sensed temperatures at a particular moment of time.

10. The apparatus as set forth in claim 9 wherein said temperature sensing means comprises a first sensor disposed within said first conduit and a second sensor disposed within said second conduit, said first and second sensors being coupled to said calculating means.

11. The apparatus as set forth in claim 10 wherein said thermoelectric cooling device is thermally coupled to a unitary heat transfer block.

12. The apparatus as set forth in claim 11 wherein said unitary heat transfer block includes a flow passage formed therein and connected to said first and second conduits at its ends.

13. The apparatus as set forth in claim 12 wherein said unitary heat transfer block further includes a third sensor disposed within said flow passage for sensing the temperature of said fluid flowing within said flow passage.

14. The apparatus as set forth in claim 13 wherein said modifying means comprises a microprocessor coupled to said first, second and third sensors.

15. The apparatus as set forth in claim 14 wherein said powering means comprises a power supply, the output of which is modulated by a pulse width modulator coupled to a shift register, and said microprocessor is coupled to said shift register for comparing the temperatures of said fluid in each of said first and second conduits and said flow passage and modifying said power supply output to said cooling device based on said comparison.

16. An improved system for regulating the temperature of a fluid circulating through a fluid flow circuit including a blanket having a fluid passage formed therein for applying a temperature to an object disposed thereagainst, said blanket including a first conduit for receiving a flow of temperature control fluid and a second conduit for discharging said flow, and said improvement comprising:
   a thermally conductive unitary block disposed within said flow circuit and having a fluid flow passage integrally formed therein with an inlet and an outlet coupled to said conduits;
   at least one thermoelectric cooling device thermally coupled to said thermally conductive unitary block, said thermoelectric cooling device having a cold side and a hot side when powered by electricity;

means for sensing the temperature of said fluid flowing in each of said conduits;

means associated with said sensing means for calculating from said sensed temperatures an indication of the temperature of said fluid flowing within said blanket; and means associated with said calculating means and said thermal block for modifying the temperature of said fluid flowing in said fluid flow passage by controlling the pulse width modulation of the power supplied to said thermoelectric cooling device.

17. The apparatus as set forth in claim 16 wherein said unitary block includes a sensor disposed within said fluid flow passage for measuring the temperature of said fluid flowing therein.

18. The apparatus as set forth in claim 17 wherein said thermoelectric cooling device is mounted on a thermally insulated plate, said thermally insulated plate being affixed to said thermally conductive unitary block.

19. The apparatus as set forth in claim 16 wherein said calculating means comprises means for adding a select set-off value to said sensed temperature of said fluid flowing within one of said conduits.

20. The apparatus as set forth in claim 19 wherein said fluid flowing within one of said conduits comprises said fluid returning from said blanket to said thermally conductive unitary block within said second conduit and said set-off value comprises an experimentally determined value.

21. The apparatus as set forth in claim 16 wherein said temperature modifying means includes a microprocessor.

22. The apparatus as set forth in claim 21 wherein said thermoelectric cooling device is coupled to a power supply, the output of which is modulated by a pulse width modulator controlled by said microprocessor.

23. The apparatus as set forth in claim 22 wherein said pulse width modulator is coupled to a shift register which is used by said microprocessor for controlling the pulse width modulation of said modulator.

24. The apparatus as set forth in claim 16 wherein said fluid flow passage comprises a plurality of interconnected flow channels disposed in generally parallel spaced relationship.

25. The apparatus as set forth in claim 24 wherein said thermally conductive unitary block further includes means for sensing the temperature of said fluid flowing within said fluid flow passage.

26. The apparatus as set forth in claim 25 wherein said thermally conductive unitary block is in direct thermal contact with said thermoelectric cooling device.

27. The apparatus as set forth in claim 16 wherein said calculating means comprises means for calculating an indication of the mean value of said sensed temperatures at a particular moment in time.

28. The apparatus as set forth in claim 27 wherein said temperature sensing means comprises a first sensor disposed within said first conduit and a second sensor disposed within said second conduit, said first and second sensors being coupled to said calculating means for calculating said indication of the mean value.

29. The apparatus as set forth in claim 28 wherein said temperature modifying means comprises a power supply, the output of which is modulated by a pulse width modulator coupled to a shift register, and a microprocessor coupled to said shift register for comparing the temperatures of said fluid in each of said first and second conduits and said flow passages and modifying said power supply output to said thermoelectric cooling device based on said comparison.

* * * * *